(12) United States Patent
Khashayar

(10) Patent No.: US 7,509,831 B2
(45) Date of Patent: Mar. 31, 2009

(54) METHOD FOR DETERMINING A PRESSURE THAT CORRESPONDS TO A FLOW RATE THROUGH A CHECK VALVE

(75) Inventor: Amir H. Khashayar, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 105 days.

(21) Appl. No.: 11/753,975

(22) Filed: May 25, 2007

(65) Prior Publication Data

US 2008/0289398 A1 Nov. 27, 2008

(51) Int. Cl.
    A61M 39/24 (2006.01)
(52) U.S. Cl. .......................... 73/1.72; 73/1.58; 73/1.71
(58) Field of Classification Search .................. 73/1.57, 73/1.58, 1.71, 1.72, 1.73, 1.74
    See application file for complete search history.

(56) References Cited

U.S. PATENT DOCUMENTS

| | | | | |
|---|---|---|---|---|
| 4,694,693 A | * | 9/1987 | Gerlowski | .................... 73/168 |
| 4,832,575 A | * | 5/1989 | Miller et al. | ................... 417/18 |
| 5,794,659 A | * | 8/1998 | DuRoss et al. | .............. 137/597 |
| 6,409,146 B1 | * | 6/2002 | Van Essen | ............... 251/149.1 |
| 6,564,615 B1 | * | 5/2003 | Carter | ......................... 73/49.2 |
| 7,401,494 B2 | * | 7/2008 | Kim et al. | ..................... 73/1.72 |
| 2005/0261715 A1 | | 11/2005 | Boukhny et al. | |
| 2007/0028665 A1 | * | 2/2007 | Kim et al. | ..................... 73/1.72 |
| 2007/0028676 A1 | * | 2/2007 | Baird et al. | ................... 73/49.7 |

* cited by examiner

Primary Examiner—David A. Rogers
(74) Attorney, Agent, or Firm—Russell Henrichs

(57) ABSTRACT

The present invention accommodates differences in cracking pressures between check valves by determining a pressure on the input of a check valve that corresponds to a predetermined flow rate at the output of the check valve. A container is incrementally pressurized and the vacuum at a point on the output side of the check valve is monitored. Once fluid begins to pass through the check valve, the vacuum drops. At the predetermined flow rate, the pump cannot maintain a predetermined vacuum level since it cannot exceed a maximum speed. At this point the pressure applied to the container corresponds to the predetermined flow rate. An offset is added to the pressure to determine the minimum operating pressure.

18 Claims, 5 Drawing Sheets

METHOD FOR DETERMINING A PRESSURE THAT CORRESPONDS TO A FLOW RATE THROUGH A CHECK VALVE

TECHNICAL FIELD

This invention relates in general to cataract lens removal using fluidic pulses, and more particularly to determining the pressure that causes a predetermined flow rate through a check valve in a liquefaction handpiece and using the pressure to control the flow of injection fluid during lens removal.

BACKGROUND

One type of surgical handpiece used in cataract surgery uses water-jet based liquefaction devices that generate pulses of heated surgical solution, which delaminate and separate lens tissue. The surgical solution or injection fluid is typically a sterile heat balanced salt solution. Pulses of injection fluid are delivered through a smooth polymer tip into the eye. The surgeon controls the pulses of injection fluid using controls that are typically provided on a console, the handpiece, or a foot pedal. For example, the surgeon can control the pulse strength by altering volume and velocity, varying the pulse rate, activating burst modes that use variable rest intervals, and/or decreasing repulsion of nuclear material.

One of the keys to controlling the injection fluid pulses is controlling the pneumatic pressure of the container that supplies the injection fluid to the handpiece since the pressure of the container is a key factor that determines the flow rate of the injection fluid through the handpiece engine and tip. In one system an internal adaptive PID pressure controller loop regulates and maintains the pressure of the container.

The injection fluid flows from the container through a length of tubing to the handpiece. Inside the handpiece is a spring and ball that together construct a check valve. The check valve prevents the pressure that is built up inside the handpiece engine from moving the injection fluid back upstream. The cracking pressure of the check valve is the minimum upstream pressure at which the valve will operate, i.e., allow fluid to flow through the check valve. Knowing the cracking pressure of the check value allows the system to control the pressure of the container that supplies the injection fluid so that the optimum flow of injection fluid is provided. In a spring and ball check valve, the cracking pressure of the check valve is determined largely by the stiffness of the spring. Since the stiffness of the spring can vary from check value to check valve, there is a need for determining the pressure that provides a certain flow rate for each check valve and using the determined pressure to control the pressure of the injection fluid container during surgical operation to achieve optimum handpiece performance.

SUMMARY

The present invention meets the needs described above by providing a method for determining a pressure on the input of a check valve that corresponds to a predetermined flow rate at a point on the output side of the check valve. The method is applied to a check valve that is installed in a handpiece and uses the existing system components to determine the pressure that corresponds to the predetermined flow rate.

Prior to the present invention, the minimum operating pressure was determined based on an assumed cracking pressure for the check valve as determined by the stiffness of the material used to form the spring and the number of turns of the spring. If the actual cracking pressure differed from the assumed or theoretical cracking pressure, then the system would pressurize the container and expect a certain flow rate, but the actual flow rate would differ. This resulted in suboptimum performance. The present invention determines the operating pressure based on the determination of the pressure that corresponds to the predetermined flow rate so that the system can more accurately control the flow rate and can provide optimum performance.

During a set-up phase, the fluidics module increases the pump speed until it determines that a predetermined vacuum is present at the tip. Once the vacuum is steady, the liquefaction control module incrementally pressurizes the injection fluid container. At each pressure level, the fluidics module monitors the vacuum at the tip. If the vacuum begins to drop, the fluidics module increases the pump speed, but does not exceed a predetermined maximum pump speed. At some point the cracking pressure of the check valve is reached and fluid begins to pass through the check valve. Once the injection fluid is flowing through the tip at a rate close to the maximum pump speed, the pump cannot maintain the predetermined vacuum. At this point the liquefaction control module determines that the pressure applied to the injection fluid container corresponds to the predetermined flow rate. An offset is added to the pressure to determine the minimum operating pressure.

These and other aspects, features and advantages of the present invention may be more clearly understood and appreciated from a review of the following detailed description of the disclosed embodiments and by reference to the appended drawings and claims.

DETAILED DESCRIPTION

The present invention is directed to determining the pressure that provides a predetermined flow rate for a specific check valve in a handpiece and using the pressure to control the operating pressure during lens removal. Briefly described, the pressure that corresponds to the predetermined flow rate is determined during a set-up phase by increasing the pressure on the injection fluid container and monitoring the vacuum at the tip of the handpiece. The pressure is used to determine a minimum operating pressure for the injection fluid container during surgical operation.

Exemplary Operating Environment

Figure 1:
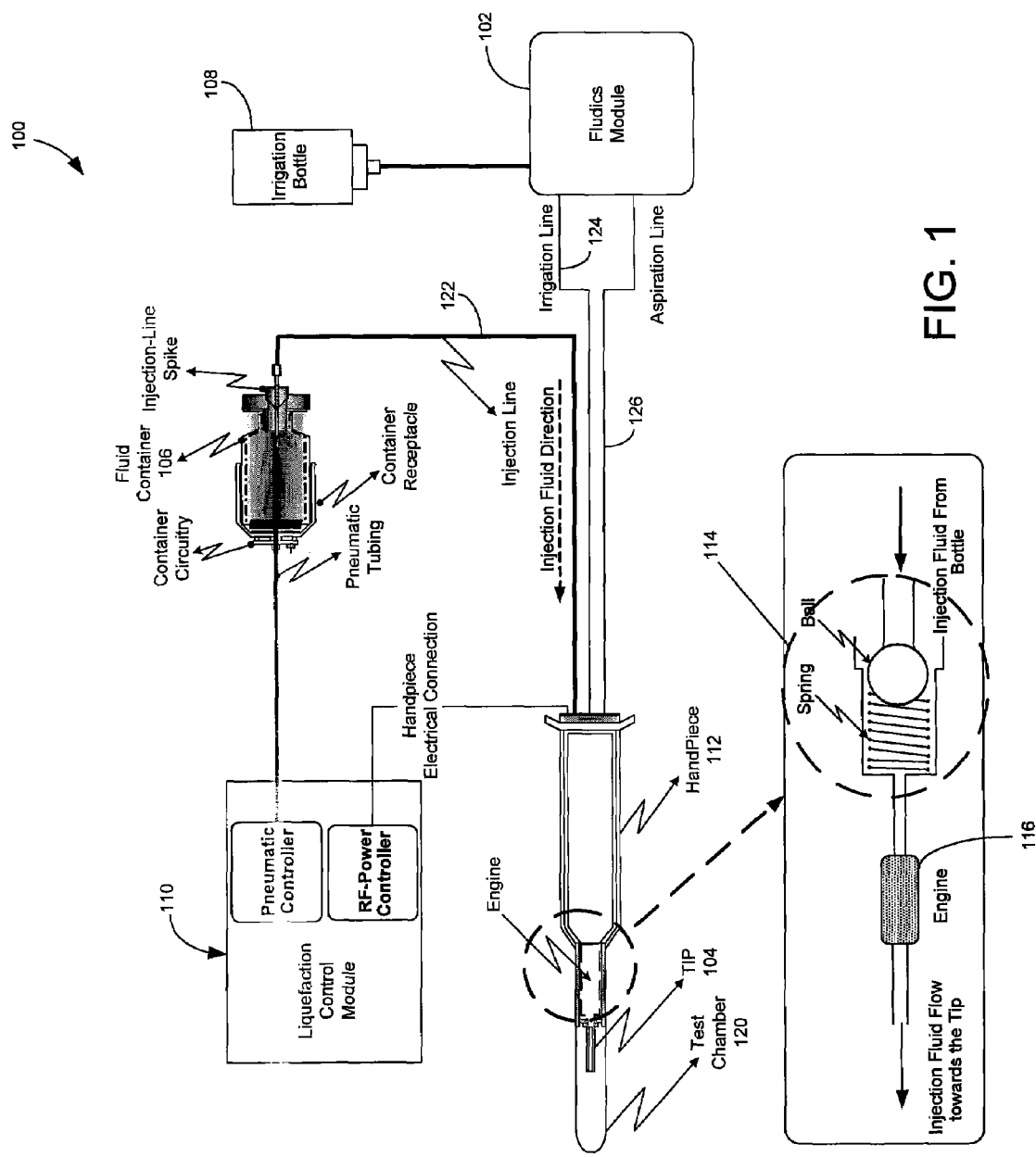
FIG. 1 is a block diagram of a lens removal system in accordance with an embodiment of the invention.

FIG. 1 illustrates an exemplary operating environment for the invention. A lens removal system 100 generates pulses of a heated surgical solution, which are used to delaminate and separate lens tissue. The surgical solution is typically a balanced salt solution referred to herein as the injection solution. One such system is the INFINITI Vision System fitted with the AQUALASE Liquefaction Device, both offered by Alcon Laboratories, Inc. The system includes the subsystems or modules that are typically present in a phacoemulsification system and a liquefaction device, which are well-known to those skilled in the art. For simplicity only certain modules of the system and the handpiece are illustrated in FIG. 1. However, additional or alternative modules can be included.

The handpiece includes a tip 104, such as a polymer tip, and is connected to an aspiration line 126, an injection line 122 and an irrigation line 124. The aspiration line carries fluid that is drawn from the eye by a vacuum, the injection line delivers the injection fluid from the injection fluid container 106 to the handpiece, and the irrigation line delivers irrigation fluid from the irrigation container 108 to the handpiece. During operation, an irrigation sleeve (not shown) is placed over the tip and the tip is placed within a cataract in the eye so that the heated pulses are propelled through the tip and at the cataract. The irrigation fluid is delivered to the eye through the irrigation sleeve and flushes the cataractous material that is removed or broken by the heated pulses from the eye.

The handpiece also includes a handpiece engine 116 and a check valve 144. The check valve is a ball and spring type valve. The injection fluid enters the handpiece and if the check valve is open, passes into the handpiece engine. The handpiece engine heats the injection fluid and generates pulses of heated injection fluid. The pulses of heated injection fluid flow from the handpiece engine towards the tip of the handpiece. The check valve prevents the fluid from flowing back upstream towards the injection line. The RF-Power controller within the liquefaction control module 110 and the handpiece engine control the timing and energy level of the pulses of heated injection fluid that are delivered to the tip.

The fluidics module 102 controls irrigation and aspiration functions of the system by controlling a pump (not shown) and monitoring the vacuum at the tip 104. Additional control functions are provided by liquefaction control module 110, which includes a pneumatic controller for controlling the pneumatic pressure on the injection fluid container using a PID pressure controller algorithm and an RF-power controller for controlling the energy delivered to the handpiece. The energy to the handpiece varies based on the type of operation (e.g., set-up or operation) and received user input (e.g., inputs from the surgeon during operation). Additional details about the fluidics module and the functions provided by one embodiment of the system are described in U.S. Pub. No. 2005/0261715, Ser. No. 11/189,492, entitled "Method of Controlling a Surgical System Based on a Load on a Cutting Tip of a Handpiece," which is incorporated herein by reference.

Determining Pressure that Corresponds to a Predetermined Flow Rate

The pressure that corresponds to a predetermined flow rate is determined during a set-up or tuning phase that occurs prior to surgical operation. A new injection fluid container and a new tip are installed for each surgery. Once the new components are installed, the user or the system initiates the set-up phase. Typically, the set-up phase occurs once per surgery, but if a problem is detected during the set-up phase or during surgery that requires the replacement of the injection fluid container, then the set-up phase may occur more frequently. The determination of the pressure that corresponds to the predetermined flow rate is one of several tests or calibrations that are executed during the set-up phase. The determination uses the existing modules and components of the system so that an existing system can be easily modified to add pressure determination to its existing set-up program.

During the set-up phase, the irrigation sleeve and a test chamber are installed at the tip of the handpiece, which provides a closed environment and simulates the insertion of the tip into the eye. FIG. 1 illustrates the test chamber 120 installed at the tip of the handpiece 104 (the irrigation sleeve is not shown). In one embodiment, the test chamber is a poly urethane boot which resembles a balloon and which covers the tip of the handpiece, including the irrigation sleeve. The fluidics module is programmed to maintain a predetermined vacuum during the set-up phase without exceeding a predetermined maximum pump rate. The system initially pressurizes the injection fluid container to a fixed low value and then incrementally increases the pressure value, but does not exceed a maximum allowable pressure. Each of the pressure values are maintained for a minimum amount of time. At each pressure value, the fluidics module monitors the vacuum at a point on the output side of the check valve, such as the tip or a point within or proximate to the handpiece engine, and communicates these values to other modules within the system, including the liquefaction control module.

Once the cracking pressure is reached, the check valve opens and fluid begins to flow through the check valve to the handpiece engine. The fluid flow through the check valve causes the vacuum to drop and the fluidics module increases the pump speed to try to maintain the predetermined vacuum. Since the pump speed is limited, at some point the pump cannot keep up with the inrush of fluid and the vacuum falls below the predetermined vacuum. The liquefaction control module monitors the vacuum values provided by the fluidics module and when the liquefaction control module determines that the vacuum has fallen below the predetermined vacuum and that the pump has reached the maximum pump speed, it determines that the current pressure corresponds to the predetermined flow rate. In some embodiments, the liquefaction control module determines that the pressure corresponds to the predetermined flow rate, when it detects a specific predetermined vacuum that is less than the predetermined vacuum.

Figure 2:
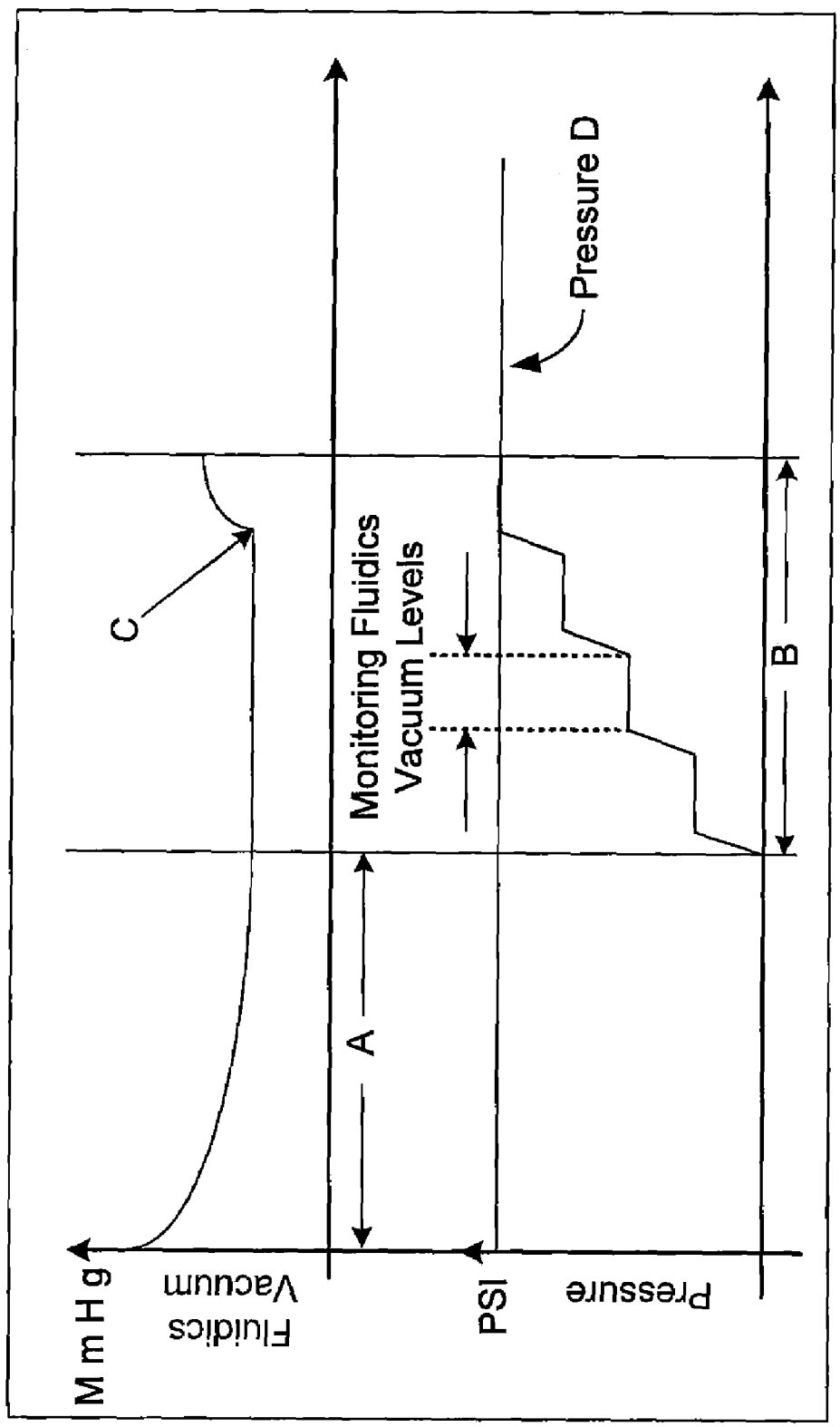
FIG. 2 is a pair of graphs illustrating the determination of the pressure that corresponds to a predetermined flow rate in accordance with an embodiment of the invention.

FIG. 2 graphically illustrates the determination of the pressure that corresponds to the predetermined flow rate for one embodiment. The top graph illustrates the vacuum over time and the bottom graph illustrates the injection fluid container pressure over time. In the first part of the graph (time period A), the fluidics module controls the pump speed until the predetermined vacuum is obtained and is steady. In the illustrated embodiment, the predetermined vacuum is approximately 50 MmHg. Once the vacuum is steady, the liquefaction control module pressurizes the injection fluid container using its internal PID pressure controller algorithm during time period B by incrementing the pressure and holding the pressure steady for a minimum amount of time. In some embodiments the same amount of time is used for each pressure level and in other embodiments, the amount of time varies between pressure levels, but is at least equal to the minimum amount of time. In the illustrated embodiment, the pressure is incremented by approximately 0.5 psi. At each pressure level, the fluidics module monitors the vacuum at the tip. If the vacuum begins to drop, the fluidics module increases the pump speed, but does not exceed a maximum pump speed of approximately 4 cc/min. At some point the cracking pressure of the check valve is reached and fluid begins to pass through the check valve. Once the injection fluid is flowing through the tip at approximately 3 cc/min, the pump cannot maintain the predetermined vacuum of approximately 50 MmHg since the maximum pump speed is approximately 4 cc/min. At this point the liquefaction control module determines that the pressure applied to the injection fluid container corresponds to the predetermined flow rate. In the illustrated embodiment the liquefaction control module determines that the predetermined flow rate is achieved at point C, which corresponds to a pressure D.

The ranges and values used to determine the pressure that corresponds to the predetermined flow rate are based on the characteristics of the components of the system. For example, the system has an operating pressure range and the injection fluid container has low and high pressure operating limits. These pressure ranges limit the pressure range that can be applied to the injection fluid container. The injection fluid container may also exhibit irregular behavior at some pressures. The resolution of the pneumatic pressure controller is limited by the system's feedback accuracy, which affects the pressure increments applied to the injection fluid container and the ability to maintain a given pressure for a certain amount of time. The accuracy of the pump rate and its repeatability also affects the ranges and values used.

Figure 3:
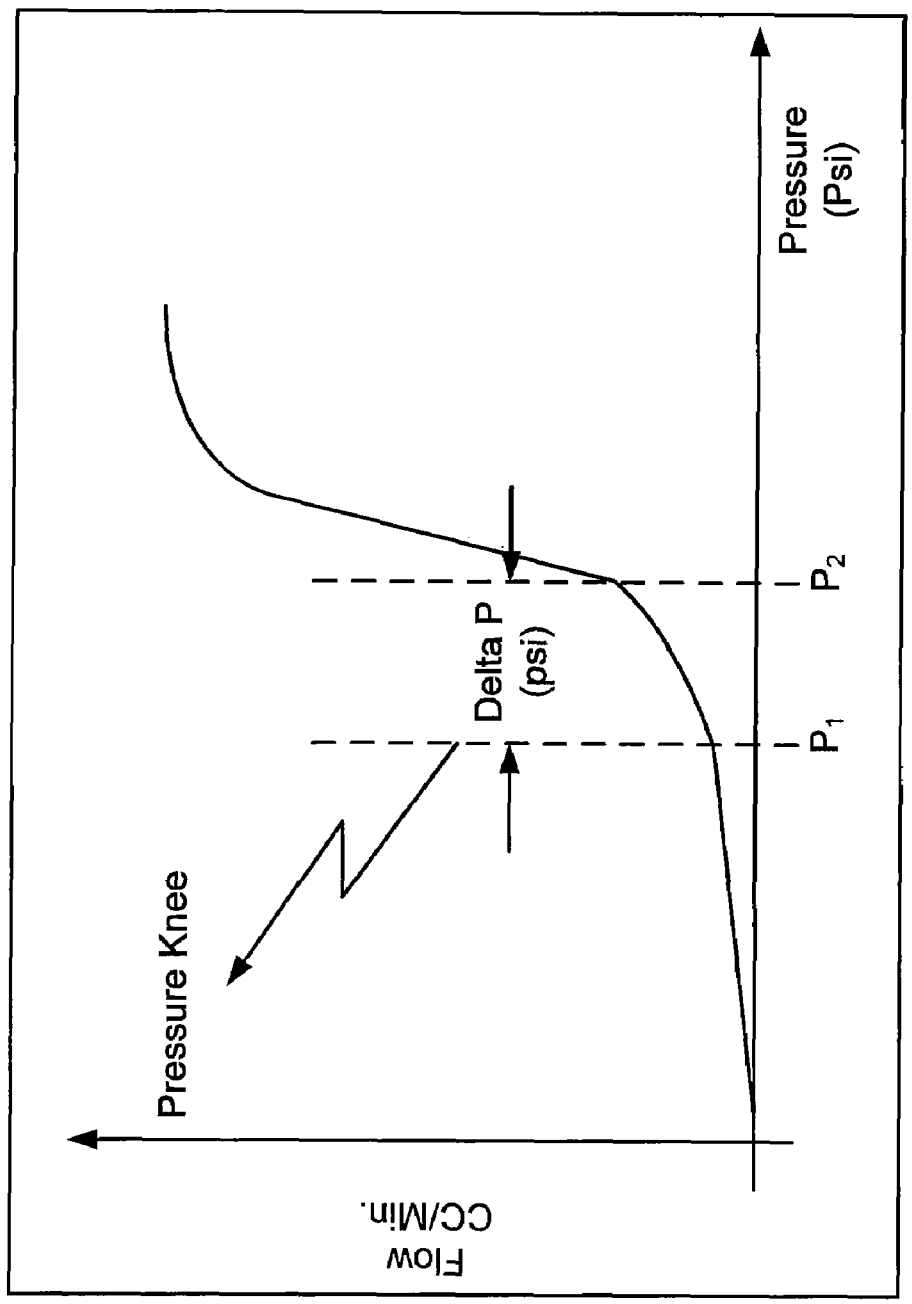
FIG. 3 is a graph illustrating the relationship between pressure and flow rate in accordance with an embodiment of the invention.

FIG. 3 provides another graphical representation of the determination of the pressure that corresponds to a predetermined flow rate. FIG. 3 illustrates how the flow rate changes as the pressure increases. Once the cracking pressure of the check valve is reached, fluid begins to flow through the check valve. In one embodiment, the system determines the pressure at the right hand side of the delta P region as the pressure that corresponds to the predetermined flow rate. Using the above example, the pressure at point P2 is the pressure that corresponds to an average flow rate of approximately 3 cc/min. Preferably, the pressure that corresponds to the predetermined flow rate corresponds to a pressure to the right of P2 that falls within the linear portion of the pressure curve.

The present invention can be implemented using software and the steps described herein can be implemented as computer-executable instructions and stored on a computer-readable medium.

Exemplary Surgical Operation

The pressure that corresponds to the predetermined flow rate directly impacts the performance of the system since it impacts the flow rate of the injection fluid during operation. Once the pressure that corresponds to the predetermined flow rate is determined, the pressure is used to determine the minimum operating pressure for the system. The minimum operating pressure is the sum of the pressure that corresponds to the predetermined flow rate and a predetermined offset. In one embodiment, the predetermined offset is between 2.0 and 2.5 psi. For example, if the pressure that corresponds to the predetermined flow rate is 2.5 psi and the predetermined offset is 2.5 psi, then the minimum operating pressure is 5.0 psi. Similarly, if the pressure that corresponds to the predetermined flow rate is 3.0 psi and the predetermined offset is 2.5 psi, then the minimum operating pressure is 5.5 psi.

Figure 4:
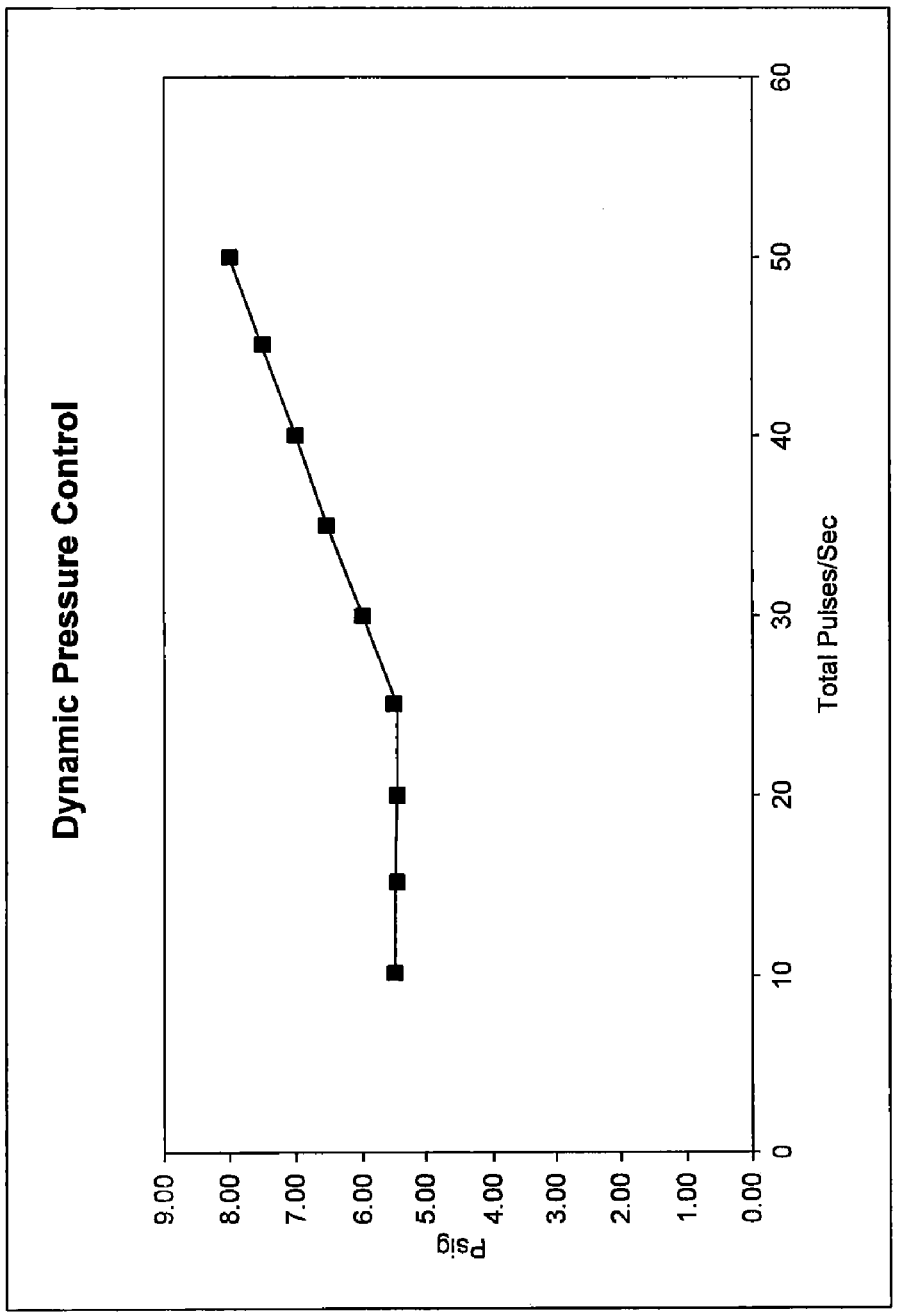
FIG. 4 is a graph illustrating the relationship between pressure and pulses/sec in accordance with an embodiment of the invention.

During surgical operation, the surgeon controls the power level. To provide additional power, the system provides more fluid, i.e., a higher flow rate. In many instances the higher flow rate requires a higher pressure on the injection fluid container. FIG. 4 illustrates the relationship between operating pressure and pulses/sec. As shown in FIG. 4 the minimum operating pressure is approximately 5.5 psi. If the surgeon requests a pulse rate between approximately 10 and 25 pulses/sec, then the operating pressure is approximately 5.5 psi. If the surgeon requests a pulse rate above approximately 25 pulses per second, then the operating pressure increases as shown. The relationship shown in FIG. 4 will be similar for other check valves and other systems. However, if the pressure that corresponds to the predetermined flow rate or the minimum operating pressure offset changes, then the pressure values will change, i.e., the line will move up or down on the graph. For example, if the minimum operating pressure is approximately 5.0 psi, then the line will move down approximately 0.5 psi, but will have the same shape.

Figure 5A:
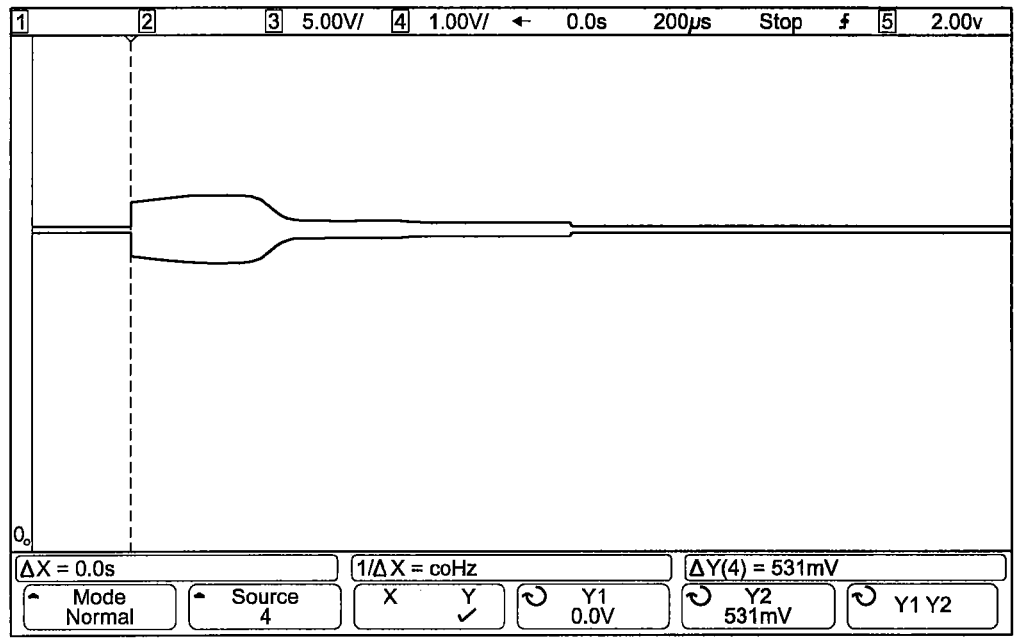
FIGS. 5A and 5B are graphs comparing handpiece energy in a system that assumes a cracking pressure and a system that determines the pressure that corresponds to a predetermined flow rate in accordance with an embodiment of the invention.
Figure 5B:
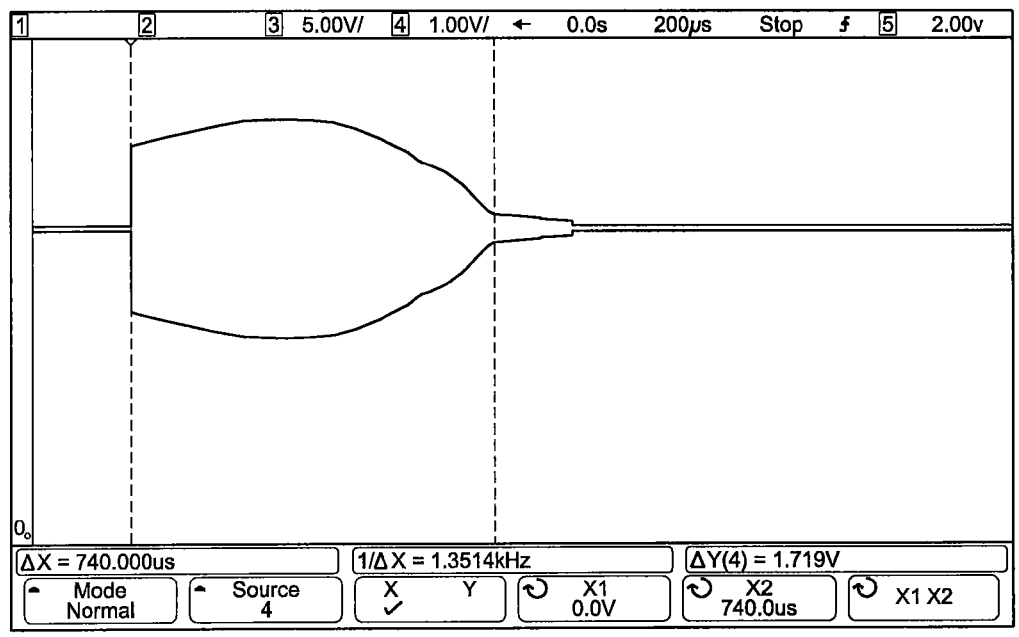

FIGS. 5A and 5B are graphs comparing handpiece energy in a system that assumes a cracking pressure and a system that determines the pressure that corresponds to a predetermined flow rate. Each of the figures illustrates the energy consumption of the handpiece during a pulse. FIG. 5A illustrates low energy consumption by the handpiece when the system assumes a value for the cracking pressure of the check valve and the assumption is incorrect. FIG. 5B illustrate normal energy consumption by the handpiece when the present invention is used to determine the pressure that corresponds to a predetermined flow rate and the pressure is used to determine the operating pressure for the system. A comparison of FIGS. 5A and 5B shows the improved energy consumption of the handpiece when the system determines the pressure that corresponds to a predetermined flow rate and uses the pressure to control the operating pressure for the system.

Additional alternative embodiments will be apparent to those skilled in the art to which the present invention pertains without departing from its spirit and scope. For example, the values used herein are for illustrative purposes only and additional and alternative values can be used or alternative measurements can be made, such as monitoring pressure rather than vacuum. The description of the functions performed by the various modules of the system herein is provided for illustrative purposes only and the functions can be performed by different modules or the modules can be configured differently in other embodiments. Accordingly, the scope of the present invention is described by the appended claims and is supported by the foregoing description.

What is claimed is:

1. A method for determining a minimum operating pressure of a hand piece, comprising:
    incrementally pressurizing a container that holds fluid that flows into an input of a check valve and monitoring vacuum at a point on an output side of the check valve;
    adjusting a pump speed to maintain a predetermined vacuum level at the point on the output side of the check valve;
    determining if the current pressure applied to the container corresponds to a predetermined flow rate once the vacuum at the point on the output side of the check valve falls below the predetermined vacuum level and the pump speed reaches a predetermined maximum pump speed; and
    determining the minimum operating pressure of the hand piece by adding a predetermined offset to the pressure that corresponds to the predetermined flow rate.

2. The method of claim 1, wherein incrementally pressurizing a container, adjusting a pump speed and determining that the current pressure corresponds to a predetermined flow rate occur during a set-up phase and a test chamber is installed at a tip of a handpiece prior to the set-up phase.

3. The method of claim 1, further comprising:
    receiving a requested power level for a hand piece engine; and
    determining an operating pressure that corresponds to the requested power level, wherein the operating pressure is greater than or equal to the minimum operating pressure.

4. The method of claim 1, wherein the vacuum at the point on the output side of the check valve is determined to have fallen below the predetermined vacuum level when the vacuum falls below a second predetermined vacuum level.

5. The method of claim 1, wherein incrementally pressurizing a container comprises:
controlling the pressure on the container so that a first incremental pressure is increased by a predetermined amount to a second incremental pressure.

6. The method of claim 1, wherein monitoring vacuum at a point on an output side of the check valve comprises observing vacuum at a tip of a handpiece.

7. The method of claim 1, wherein monitoring vacuum at a point on an output side of the check valve comprises observing vacuum within a handpiece engine.

8. A method for determining an operating pressure of a hand piece, comprising:
during a set-up phase, determining a pressure that corresponds to a predetermined flow rate by:
installing a test chamber at a tip of a handpiece;
controlling a pump to obtain a predetermined vacuum level at a point on an output side of a check valve;
pressurizing a container that holds fluid that flows into an input of the check valve to an initial pressure;
monitoring vacuum at the point on the output side of the check value;
if the vacuum corresponds to the predetermined vacuum level, then increasing the initial pressure by an increment until the pump reaches a maximum speed and the monitored vacuum falls below the predetermined vacuum level;
determining if the current pressure applied to the container corresponds to the predetermined flow rate once the pump reaches a maximum speed and the monitored vacuum is below the predetermined vacuum level; and
removing the tip of the handpiece from the test chamber; and
during operation:
receiving a requested power level for a hand piece engine; and
determining an operating pressure of the hand piece to achieve the requested power level, wherein the operating pressure is based on the pressure that corresponds to the predetermined flow rate.

9. The method of claim 8, further comprising:
determining a minimum operating pressure by adding a predetermined offset to the pressure that corresponds to the predetermined flow rate; and
during operation, maintaining the operating pressure so that it is at least equal to the minimum operating pressure.

10. The method of claim 8, wherein monitoring vacuum at the point on the output side of the check valve comprises observing vacuum at a tip of a handpiece.

11. The method of claim 8, wherein monitoring vacuum at the point on the output side of the check valve comprises observing vacuum within a handpiece engine.

12. The method of claim 8, wherein the monitored vacuum is below the predetermined vacuum level when the monitored vacuum falls below a second predetermined vacuum level.

13. A method for determining an operating pressure of a hand piece, comprising:
determining a pressure that corresponds to a predetermined flow rate by:
controlling a pump to obtain a predetermined vacuum level at a point on an output side of a check valve;
incrementally pressurizing a container that holds fluid that flows into an input of the check valve by increasing the pressure on the container through a plurality of pressure levels;
monitoring vacuum at the point on the output side of the check value for each pressure level; and
determining if the current pressure applied to the container corresponds to the predetermined flow rate once the pump reaches a predetermined maximum speed and the monitored vacuum remains below the predetermined vacuum level; and
using the pressure that corresponds to the predetermined flow rate to determine the operating pressure of the hand piece.

14. The method of claim 13, further comprising:
determining a minimum operating pressure by adding an offset to the pressure that corresponds to the predetermined flow rate.

15. The method of claim 13, wherein a test chamber is used for determining a pressure that corresponds to a predetermined flow rate.

16. The method of claim 13, wherein the check valve is located in a handpiece and the point on the output side of the check valve is a tip of the handpiece.

17. The method of claim 13, wherein the check valve is located in a handpiece and the point on the output side of the check valve is within a handpiece engine.

18. The method of claim 13, wherein a subsequent one of the pressure levels is a predetermined amount higher than a previous one of the pressure levels.

* * * * *